United States Patent
Je et al.

(10) Patent No.: US 11,552,715 B2
(45) Date of Patent: Jan. 10, 2023

(54) BODY CHANNEL COMMUNICATION METHOD AND APPARATUS FOR PERFORMING THE SAME

(71) Applicant: KOREA ADVANCED INSTITUTE OF SCIENCE AND TECHNOLOGY, Daejeon (KR)

(72) Inventors: Minkyu Je, Daejeon (KR); Yeseul Jeon, Daejeon (KR); Chongsoo Jung, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 16/891,550

(22) Filed: Jun. 3, 2020

(65) Prior Publication Data
US 2020/0389235 A1   Dec. 10, 2020

(30) Foreign Application Priority Data

Jun. 7, 2019   (KR) .................. 10-2019-0067259
Jan. 9, 2020   (KR) .................. 10-2020-0002925

(51) Int. Cl.
*H04B 13/00*   (2006.01)
*G05B 19/4155*   (2006.01)

(52) U.S. Cl.
CPC ....... *H04B 13/005* (2013.01); *G05B 19/4155* (2013.01); *G05B 2219/31305* (2013.01); *G05B 2219/40264* (2013.01)

(58) Field of Classification Search
CPC .................................................. H04B 13/005
See application file for complete search history.

(56) References Cited

U.S. PATENT DOCUMENTS

| 3,883,900 A | * | 5/1975 | Jerard | A61F 2/72 623/60 |
| 4,976,264 A | * | 12/1990 | Petrofsky | A61N 1/36003 607/48 |
| 2009/0030530 A1 | * | 1/2009 | Martin | A61B 5/4851 623/53 |
| 2011/0307079 A1 | * | 12/2011 | Oweiss | A61B 5/4094 600/545 |

(Continued)

FOREIGN PATENT DOCUMENTS

| KR | 20090102943 A | 10/2009 | |
| WO | WO-2008042900 A2 | * 4/2008 | ........... A61B 5/0031 |

OTHER PUBLICATIONS

A 100Mb/s Galvanically-Coupled Body-Channel-Communication Transceiver with 4.75pJ/b TX and 26.8 pJ/b RX for Bionic Arms; 2017; School of EE, KAIST, Yuseong-Gu, Daejeon, Republic of Korea; 2017. 2 pages. Abstract.

(Continued)

*Primary Examiner* — Hsinchun Liao
(74) *Attorney, Agent, or Firm* — Christensen, Fonder, Dardi & Herbert PLLC; John Fonder

(57) ABSTRACT

Disclosed are a body channel communication method and an apparatus performing the same. An operating method of a transmitter includes obtaining an input signal including biometric information, generating an encoded signal and a control signal by encoding the input signal, generating a return-to-zero (RZ) signal of a biphasic waveform based on the encoded signal, and transmitting the RZ signal through a body channel.

10 Claims, 23 Drawing Sheets

(56) References Cited

U.S. PATENT DOCUMENTS

| | | | | |
|---|---|---|---|---|
| 2015/0245928 | A1* | 9/2015 | Kao | G06N 3/08 |
| | | | | 700/90 |
| 2016/0207201 | A1* | 7/2016 | Herr | B62D 57/032 |
| 2019/0030339 | A1* | 1/2019 | Baru | A61B 5/686 |
| 2020/0254246 | A1* | 8/2020 | Zorman | A61N 1/37229 |
| 2022/0130134 | A1* | 4/2022 | Jansen | G06V 40/15 |

OTHER PUBLICATIONS

A 100Mb/s Galvanically-Coupled Body-Channel-Communication Transceiver with 4.75pJ/b TX and 26.8 pJ/b RX for Bionic Arms; 2017; School of EE, KAIST, Yuseong-Gu, Daejeon, Republic of Korea; 2017. 34 pages.

A Fast Phase Tracking Reference—Less All-Digital CDR Circuit for Human Body Channel Communication; Chung 2019; Microelectronics Journal 84; pp. 87-95.

Baseband Digital Modulation; 2017; 20 pages.

A 100Mb/s Galvanically-Coupled Body-Channel-Communication Transceiver with 4.75pJ/b TX and 26.8 pJ/b RX for Bionic Arms; 2017; School of EE, KAIST, Yuseong-Gu, Daejeon, Republic of Korea; Jun. 9, 2019. 34 pages.

A 100Mb/s Galvanically-Coupled Body-Channel-Communication Transceiver with 4.75pJ/b TX and 26.8 pJ/b RX for Bionic Arms; 2017; School of EE, KAIST, Yuseong-Gu, Daejeon, Republic of Korea; Jun. 9, 2019. 2 pages. Abstract.

* cited by examiner

BODY CHANNEL COMMUNICATION METHOD AND APPARATUS FOR PERFORMING THE SAME

CROSS-REFERENCE TO RELATED APPLICATION(S)

This application claims the priority benefit of Korean Patent Application No. 10-2019-0067259 filed on Jun. 7, 2019, and Korean Patent Application No. 10-2020-0002925 filed on Jan. 9, 2020, in the Korean Intellectual Property Office, the disclosures of which are incorporated herein by reference for all purposes.

BACKGROUND

1. Field of the Invention

One or more example embodiments relate to a body channel communication method and an apparatus performing the same.

2. Description of the Related Art

Communication using a body channel refers to a technique that transmits information to electrodes of a transmitter attached to a part of a human body being conductive, using the body as a communication channel, and restores the transmitted information by connecting to electrodes of a receiver attached to another part of the body or provided outside of the body.

A communication method using a body channel is a technique that enables "communication with a fixed device" to be performed through a simple contact of a user, for the purpose of communication between various portable devices such as a personal digital assistant (PDA), a portable personal computer, a digital camera, an MP3 player, and a mobile phone, or printing (communication with a printer), credit card payment, TV reception, access control (communication with an access control system), or fare payment for bus and subway rides.

SUMMARY

An aspect provides a current coupling type high-speed body channel communication technique that may alleviate the effects of environmental changes and disturbances.

According to an aspect, there is provided an operating method of a transmitter, the operating method including obtaining an input signal including biometric information, generating an encoded signal and a control signal by encoding the input signal, generating a return-to-zero (RZ) signal of a biphasic waveform based on the encoded signal and, transmitting the RZ signal through a body channel.

The encoded signal may include a first encoded signal configured to generate a positive pulse of the RZ signal, and a second encoded signal configured to generate a negative pulse of the RZ signal.

The operating method may further include performing first-order charge balancing using the RZ signal.

The operating method may further include performing passive charge balancing based on the control signal.

The generating of the RZ signal may include generating the RZ signal using a current source.

The control signal may include an activation signal configured to activate or deactivate the current source.

According to an aspect, there is provided an operating method of a receiver, the operating method including receiving an RZ signal of a biphasic waveform through a body channel, generating a squared signal by inputting the RZ signal into a square circuit, detecting an error with respect to the RZ signal, and generating restored data based on the squared signal.

The receiving may include receiving the RZ signal through an electrode including a termination.

The detecting may include determining whether positive or negative pulses are detected consecutively in the RZ signal if the error detection operation is activated.

According to an aspect, there is provided a transmitter including a memory configured to store an input signal including biometric information, an RZ encoder configured to generate an encoded signal and a control signal by encoding the input signal, a channel driver configured to generate an RZ signal of a biphasic waveform based on the encoded signal, and an electrode configured to transmit the RZ signal through a body channel.

The encoded signal may include a first encoded signal configured to generate a positive pulse of the RZ signal, and a second encoded signal configured to generate a negative pulse of the RZ signal.

The channel driver may be configured to perform first-order charge balancing using the RZ signal.

The channel driver may be configured to perform passive charge balancing based on the control signal.

The channel driver may include a current source.

The control signal may include an activation signal configured to activate or deactivate the current source.

According to an aspect, there is provided a receiver including an electrode configured to receive an RZ signal of a biphasic waveform through a body channel, a squarer configured to generate a squared signal by inputting the RZ signal into a square circuit, an error detector configured to detect an error with respect to the RZ signal, and a clock and data recovery (CDR) circuit configured to generate restored data based on the squared signal.

The receiver may further include a termination connected to the electrode.

The error detector may be configured to determine whether positive or negative pulses are detected consecutively in the RZ signal if activated.

According to an aspect, there is provided a communication system including the transmitter and the receiver.

Additional aspects of example embodiments will be set forth in part in the description, which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1A:
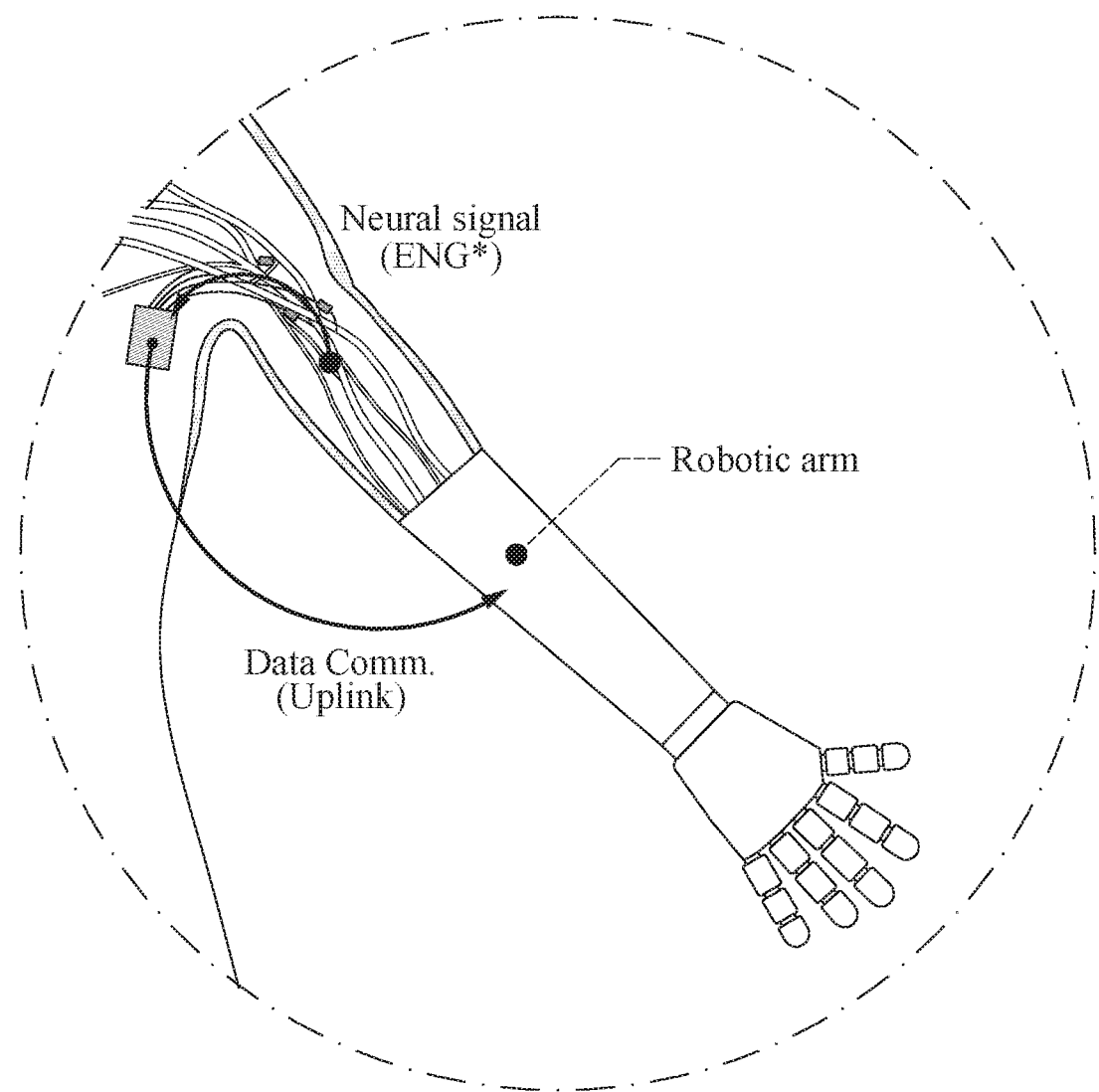
FIGS. 1A and 1B illustrate a bionic arm according to an example embodiment.

Hereinafter, example embodiments will be described in detail with reference to the accompanying drawings. However, various alterations and modifications may be made to the example embodiments. Here, the example embodiments are not construed as limited to the disclosure. The example embodiments should be understood to include all changes, equivalents, and replacements within the idea and the technical scope of the disclosure.

The terminology used herein is for the purpose of describing particular example embodiments only and is not to be limiting of the example embodiments. As used herein, the singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Terms, such as first, second, and the like, may be used herein to describe components. Each of these terminologies is not used to define an essence, order or sequence of a corresponding component but used merely to distinguish the corresponding component from other component(s). For example, a first component may be referred to as a second component, and similarly the second component may also be referred to as the first component.

Unless otherwise defined, all terms including technical and scientific terms used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the example embodiments with reference to the accompanying drawings, like reference numerals refer to like constituent elements and a repeated description related thereto will be omitted. In the description of example embodiments, detailed description of well-known related structures or functions will be omitted when it is deemed that such description will cause ambiguous interpretation of the present disclosure.

Figure 1B:
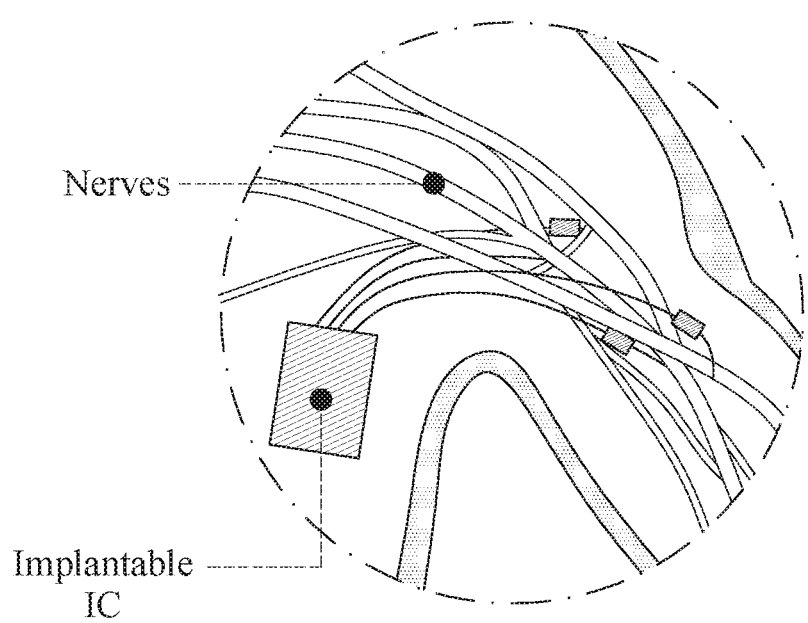

FIGS. 1A and 1B illustrate a bionic arm according to an example embodiment.

A bionic arm may be an artificial arm system that operates according to the intent of a user.

The bionic arm may include a robotic arm and an implantable IC.

The robot arm may operate according to the intent of a user. For example, the robot arm may operate based on a neural signal of the user. In this example, the neural signal may be replaced by an electromyographic (EMG) signal.

The implantable IC may detect a neural signal generated at a major peripheral nerve of the user. For example, the implantable ICs may detect neural signals generated at five major peripheral nerves.

The implantable IC may convert the detected neural signal into a digital signal. The implantable IC may transmit the digital signal to the robot arm through an uplink. For example, the IC may transmit the digital signal to the robotic arm through a body channel.

The robot arm may receive the digital signal transmitted by the implantable IC. For example, the robot arm may receive the digital signal through the body channel.

The robot arm may discern the intent of the user based on the digital signal and execute a command from the user based on the intent of the user.

There are three key requirements for the uplink of the bionic arm (or the artificial arm system).

(1) The uplink requires a high data rate (HDR) and low power consumption. The uplink of the bionic arm needs to provide an HDR over 96 Mb/s to control the robot arm with a high degree of freedom in real time. In addition, when the energy of the implantable IC is supplied by a wireless power transmission system provided in the size of 1 $cm^2$, a transmitter of the bionic arm needs to consume less than 2 mW for human-body safety.

(2) The uplink requires detachability and robustness. The bionic arm may be implemented in a detachable form for the convenience and safety of the user. Therefore, the bionic arm needs to maintain robust communication even under varying condition changes resulting from repeated reattachments. In particular, smooth communication should be ensured even if the position of an electrode or antenna changes due to reattachments, or an alignment issue occurs. In addition, the bionic arm needs to be able to perform an error detection function to prevent an unintentional operation of a robot arm.

(3) The bionic arm needs to be designed considering the human-body safety. The bionic arm is an implantable and semi-permanent device, and the bionic arm and the uplink of the bionic arm need to be designed considering the human-body safety.

Figure 2A:
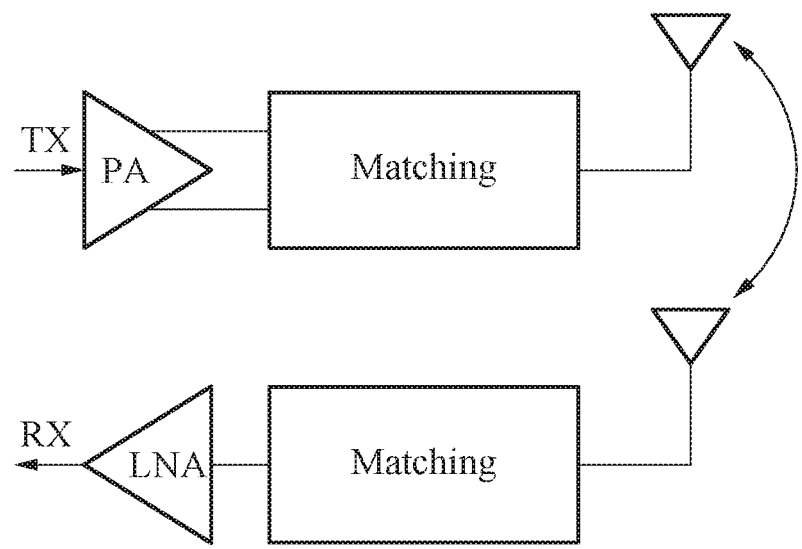
FIGS. 2A through 2C illustrate a conventional communication system applicable to a bionic arm.
Figure 2B:
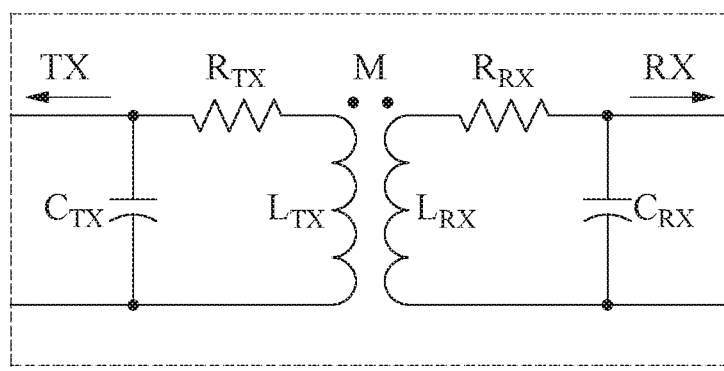
Figure 2C:
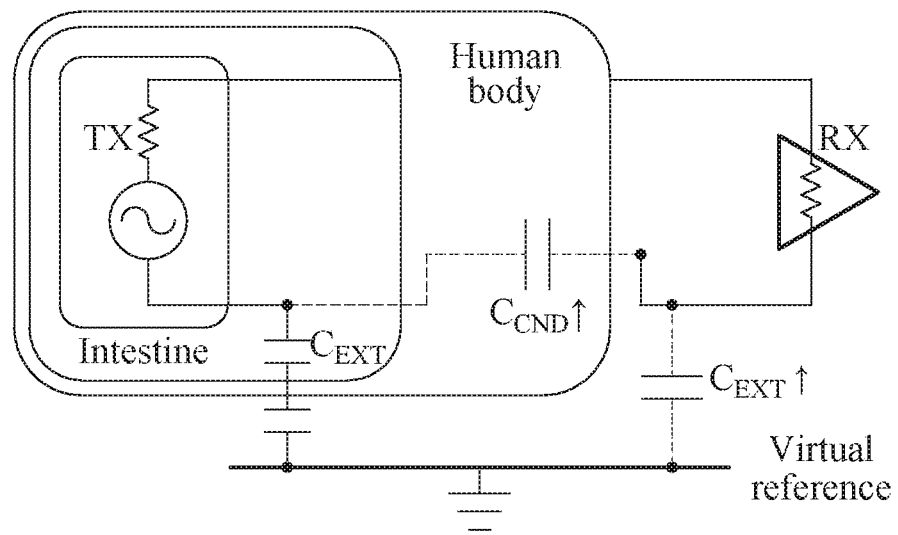

FIGS. 2A through 2C illustrate a conventional communication system applicable to a bionic arm.

FIG. 2A illustrates a medical implant communication service (MICS)/the industrial, scientific and medical (ISM). The MICS/ISM may provide robust wireless communication, but may have low data rates and lack energy efficiency.

FIG. 2B illustrates inductive coupling. A communication system using inductive coupling may provide a high data rate and energy efficiency, but have a degraded performance due to an alignment issue. In order to alleviate the alignment issue of the communication system using inductive coupling, it may be necessary to increase the physical size of the implanted inductor.

FIG. 2C illustrates capacitive coupling body channel communication (CC-BCC). CC-BCC has channel characteristics that may be greatly affected by an environment. Since an ambient environmental condition of a bionic arm is not constant, CC-BCC may not be suitable as a communication method of the bionic arm. In addition, a transmitter of CC-BCC is implemented as a voltage-mode channel driver, and thus the human-body safety may not be guaranteed.

That is, a conventional communication system may not meet the requirements for implementing a robust, high-speed and energy-efficient uplink of a bionic arm while ensuring the human-body safety.

Figure 3A:
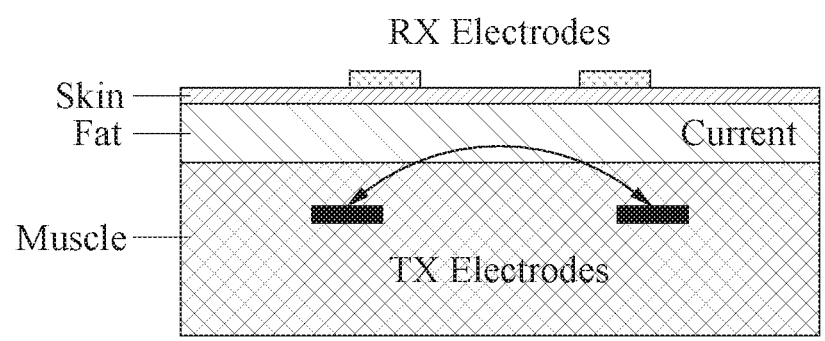
FIGS. 3A and 3B illustrate galvanically-coupled body channel communication (GC-BCC)
Figure 3B:
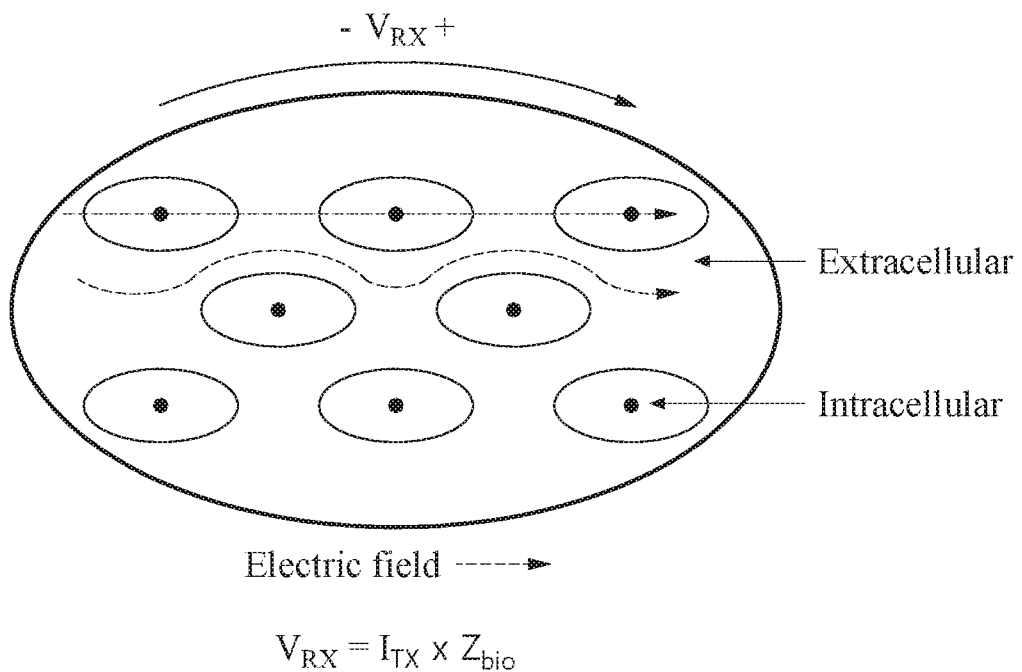

FIGS. 3A and 3B illustrate galvanically-coupled body channel communication (GC-BCC).

GC-BCC refers to body channel communication that uses a differential signal through two pairs of electrodes.

When a current flows between two electrodes of a transmitter (TX) of GC-BCC, an electric field may be induced in human tissues, and a voltage between two electrodes of a receiver (RX) may be induced. That is, in GC-BCC, bio-impedance ($Z_{bio}$) may be a channel response.

The voltage $V_{RX}$ induced to the receiver RX may be expressed by Equation 1.

$$V_{RX} = I_{TX} \times Z_{bio} \qquad \text{[Equation 1]}$$

Here, $I_{TX}$ denotes the current flowing between the two electrodes of the transmitter TX.

GC-BCC may have the following advantages over CC-BCC.

(1) GC-BCC uses bioimpedance as a communication channel, and thus the channel may be more robust and hardly affected by environmental changes.

(2) GC-BCC uses a differential signal and thus, may handle common mode interference (CM-interference). On the other hand, CC-BCC uses a single signal electrode and thus, may not handle CM-interference.

(3) GC-BCC may regulate a current applied to a human body and thus, may ensure the human-body safety.

A high-frequency electric field may penetrate a cell membrane, whereas a low-frequency electric field may not pass through a cell membrane. Thus, the bioimpedance may have a low-pass-filter characteristic. Therefore, GC-BCC may have a limited bandwidth. Conventional GC-BCC has a narrow channel bandwidth less than 10 MHz and may be difficult to increase a data rate in excess of tens of Mb/s.

Figure 4:
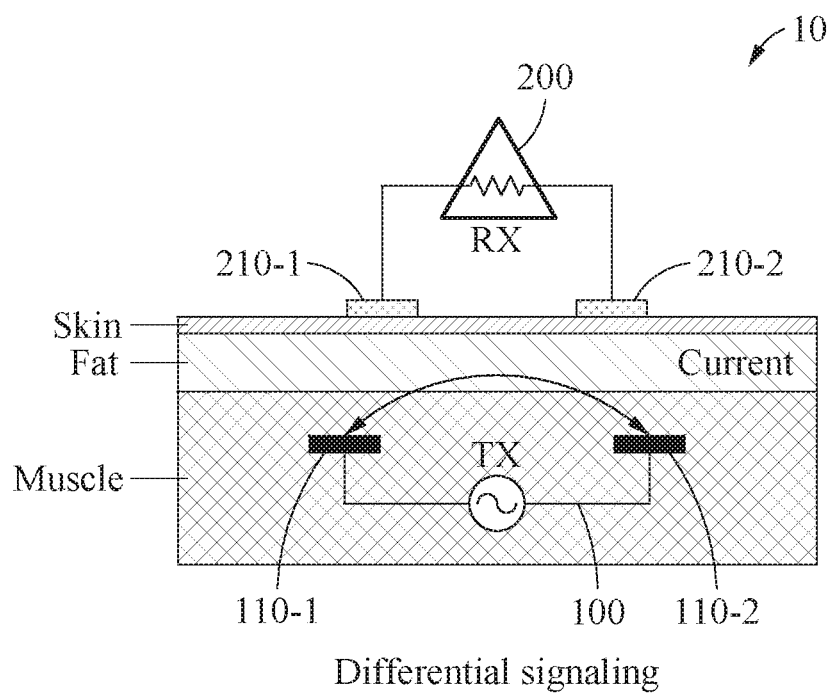
FIG. 4 illustrates a communication system through a body channel according to an example embodiment.

FIG. 4 illustrates a communication system through a body channel according to an example embodiment.

A communication system 10 through a body channel implemented with GC-BCC may be applied to a bionic arm.

An uplink of the communication system 10 may use bioimpedance as a communication channel. Therefore, the communication system 10 may be tolerable to misalignment between TX electrodes and RX electrodes.

The uplink of the communication system 10 may be implemented with wide-band GC-BCC capable of high-speed data communication. For example, the communication system 10 may perform broadband communication by adding a termination to a receiver 200.

The communication system 10 may be implemented with low power by baseband signaling through bipolar return-to-zero (RZ) coding.

In addition, the communication system 10 may consider the human-body safety and perform real-time error detection.

The communication system 10 may include a transmitter 100 and the receiver 200.

The transmitter 100 may perform bipolar RZ coding and transmit an RZ signal in a biphasic waveform to the receiver 200. For example, the transmitter 100 may transmit the RZ signal of the biphasic waveform to the receiver 200 through the uplink implemented with GC-BCC.

The transmitter 100 may be implemented as an implantable IC, and may transmit a signal to the receiver 200 through a pair of electrodes 110-1 and 110-2.

The receiver 200 may receive the RZ signal of the biphasic waveform transmitted by the transmitter 100. For example, the receiver 200 may receive the RZ signal of the biphasic waveform through the uplink implemented with GC-BCC.

The receiver 200 may include a termination in an input, thereby extending the channel bandwidth.

The receiver 200 may restore data and/or a clock signal of the signal received from the transmitter 100. For example, the receiver 200 may restore the data and/or the clock signal based on the RZ signal of the biphasic waveform.

The receiver 200 may detect an error with respect to the signal received from the transmitter 100. For example, an error in the RZ signal of the biphasic waveform may be detected.

The receiver 200 may be implemented in a robot arm detachable to a user, and may receive the signal from the transmitter 100 through a pair of electrodes 210-1 and 210-2.

Figure 5:
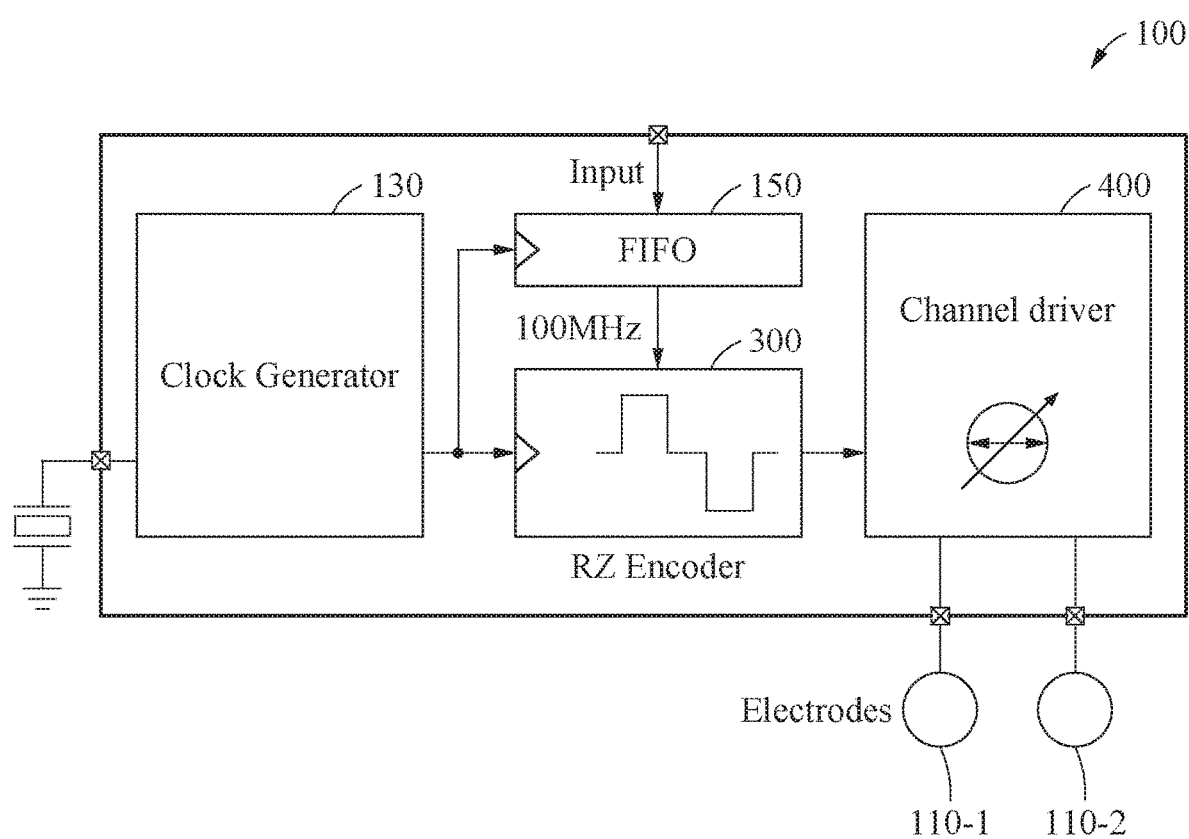
FIG. 5 is a block diagram illustrating an example of a transmitter shown in FIG. 4.

FIG. 5 is a block diagram illustrating an example of the transmitter shown in FIG. 4.

The transmitter 100 may include a pair of electrodes 110-1 and 110-2, a clock generator 130, a memory 150, an RZ encoder 300, and a channel driver 400.

The electrodes 110-1 and 110-2 may transmit a signal output from the channel driver 400. For example, the electrodes 110-1 and 110-2 may transmit the signal through a body channel. The channel driver 400 may be current-mode channel driver.

The clock generator 130 may generate a clock signal. For example, the clock generator 130 may include an injection-locked oscillator (ILO) operating as a frequency multiplier that provides a 100-MHz clock signal. The clock generator 130 may output the clock signal to the memory 150 and the RZ encoder 300.

The memory 150 may store an input signal. For example, the memory 150 may store the input signal including biometric information from the sensor.

Also, the memory 150 may output the stored input signal to the RZ encoder 300. For example, the memory 150 may synchronize the input signal with the clock signal and output the synchronized input signal to the RZ encoder 300. That is, the memory 150 may output the input signal to the RZ encoder 300 in response to the clock signal.

For example, the memory 150 may be a buffer that temporarily stores the input signal including biometric information.

The RZ encoder 300 may encode the input signal to a bipolar RZ form in response to the clock signal. For example, the RZ encoder 300 may generate encoded data (or an encoded signal) and/or a control signal to generate a biphasic RZ signal.

The channel driver 400 may generate an RZ signal of a biphasic waveform based on the encoded data and/or the control signal. For example, the channel driver 400 may transmit the RZ signal in the form of a regulated current through the body channel using the electrodes 110-1 and 110-2.

The channel driver 400 may perform charge balancing. Thus, the channel driver 400 may perform charge balancing to ensure the human-body safety.

Figure 6A:
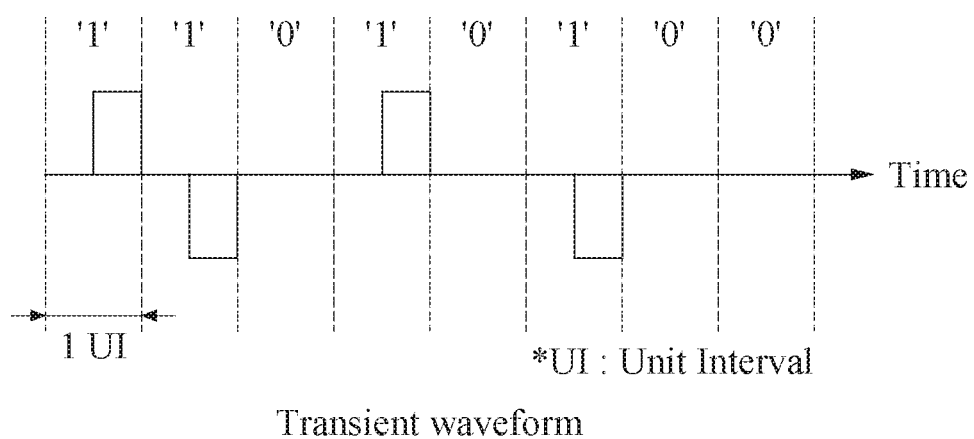
FIGS. 6A through 6C illustrate a return-to-zero (RZ) signal transmitted by the transmitter of FIG. 5.
Figure 6B:
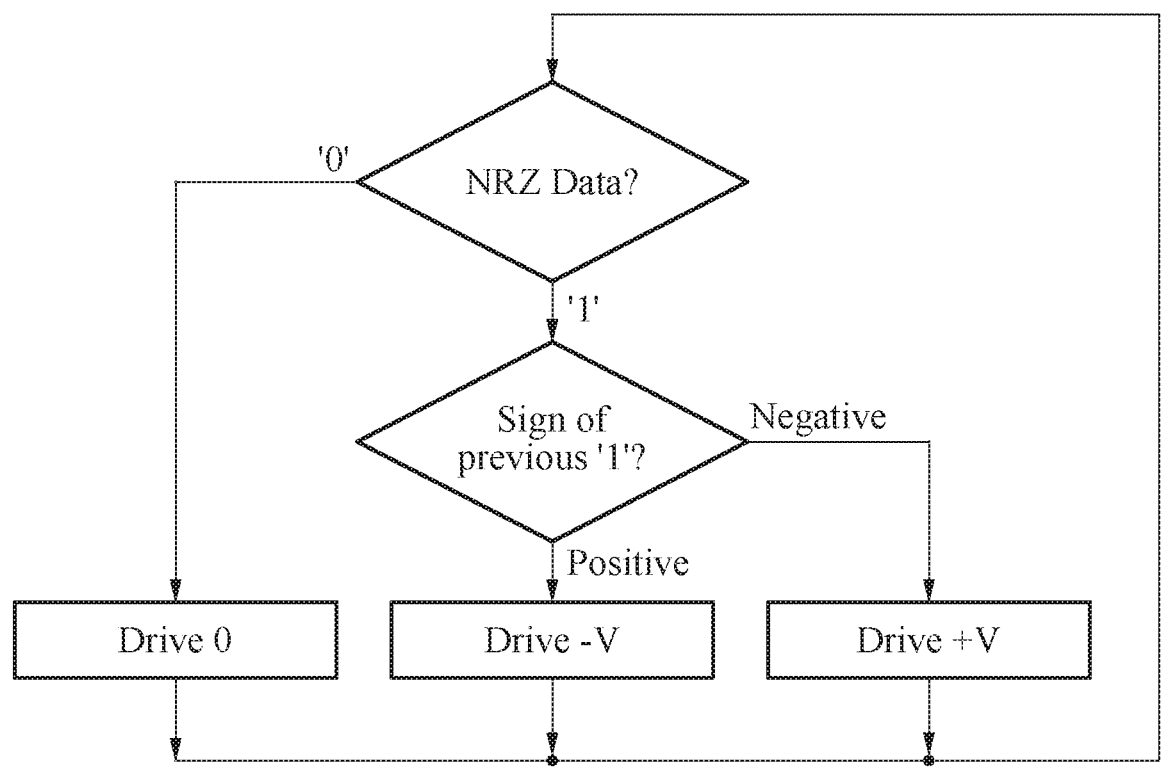
Figure 6C:
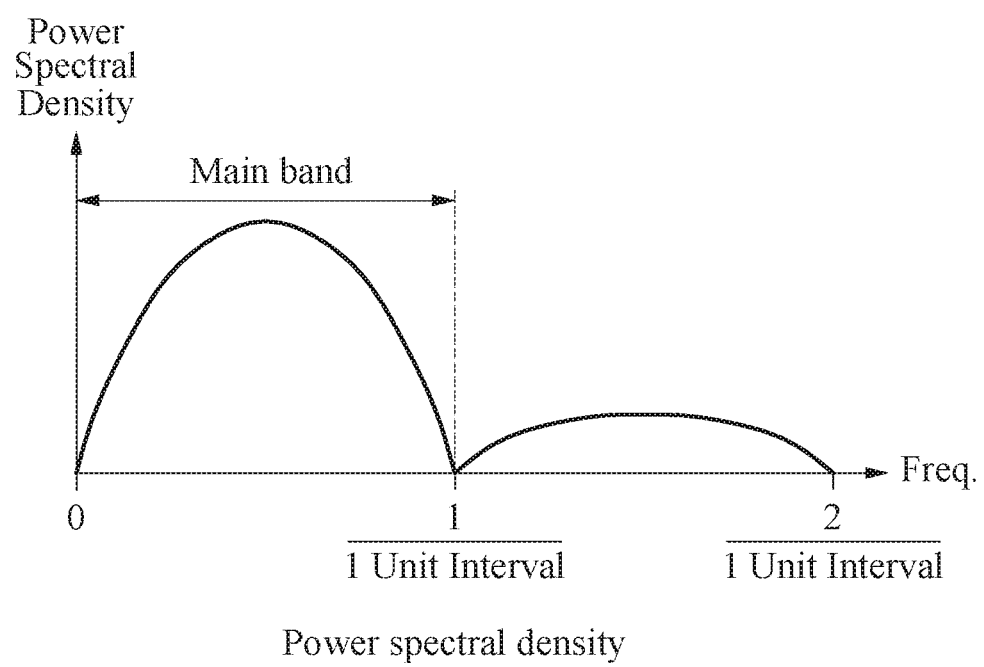

FIGS. 6A through 6C illustrate an RZ signal transmitted by the transmitter of FIG. 5.

A bipolar RZ (or a biphasic RZ) may be a line code in which a signal drops to zero between pulses.

Even if the bipolar RZ signal has a value of "1", the bipolar RZ signal may have a value of "0" for half of a unit interval and a value of "1" for the other half. That is, for half of the unit interval, the value may be always maintained as "0".

FIG. 6B illustrates an algorithm for converting a non-return-to-zero (NRZ) signal into a bipolar RZ signal. Binary "0" (zero) of an NRZ signal may be encoded as "0", and binary "1" (one) may be encoded as a positive voltage or a negative voltage. Each binary "1" of the NRZ signal may have a sign opposite to a sign of previous binary "1".

The communication system 10 may need a channel bandwidth of 100 MHz to have a data rate of 100 Mb/s. In this example, if line coding such as bipolar RZ coding is used, there is no need to generate a high carrier frequency, and a low-power system may be designed.

Figure 7:
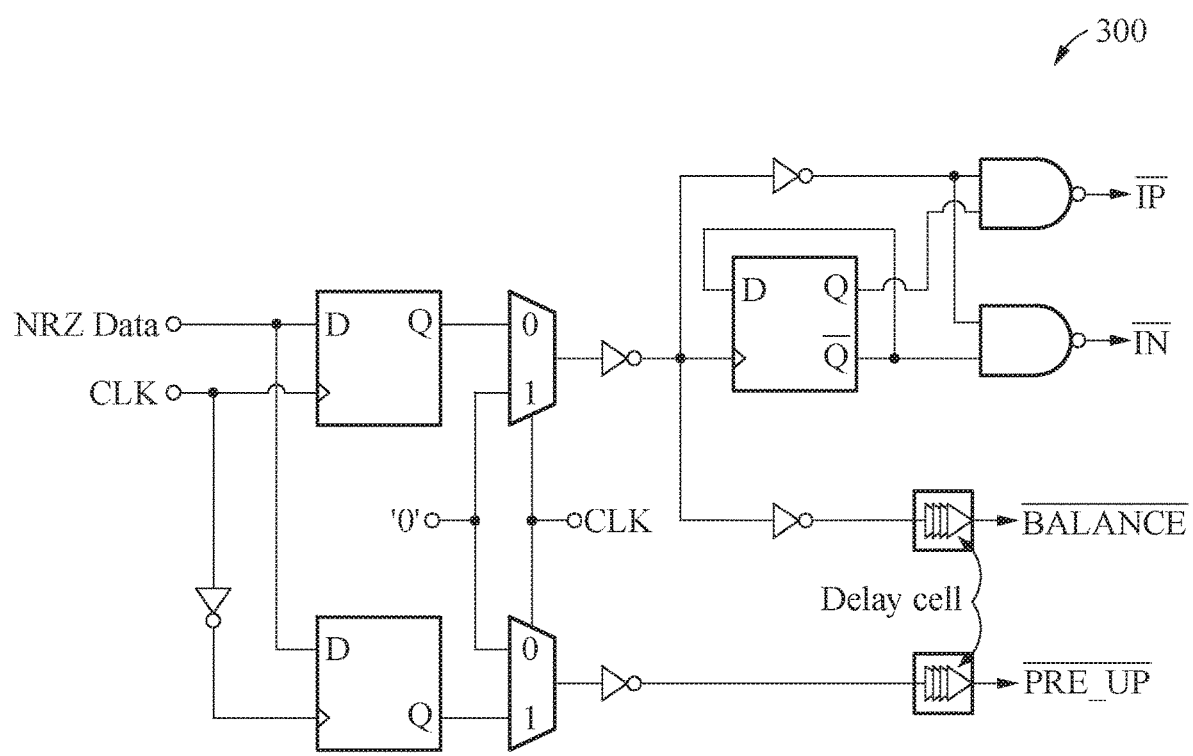
FIG. 7 is a circuit diagram illustrating an example of an RZ encoder shown in FIG. 5.
Figure 8:
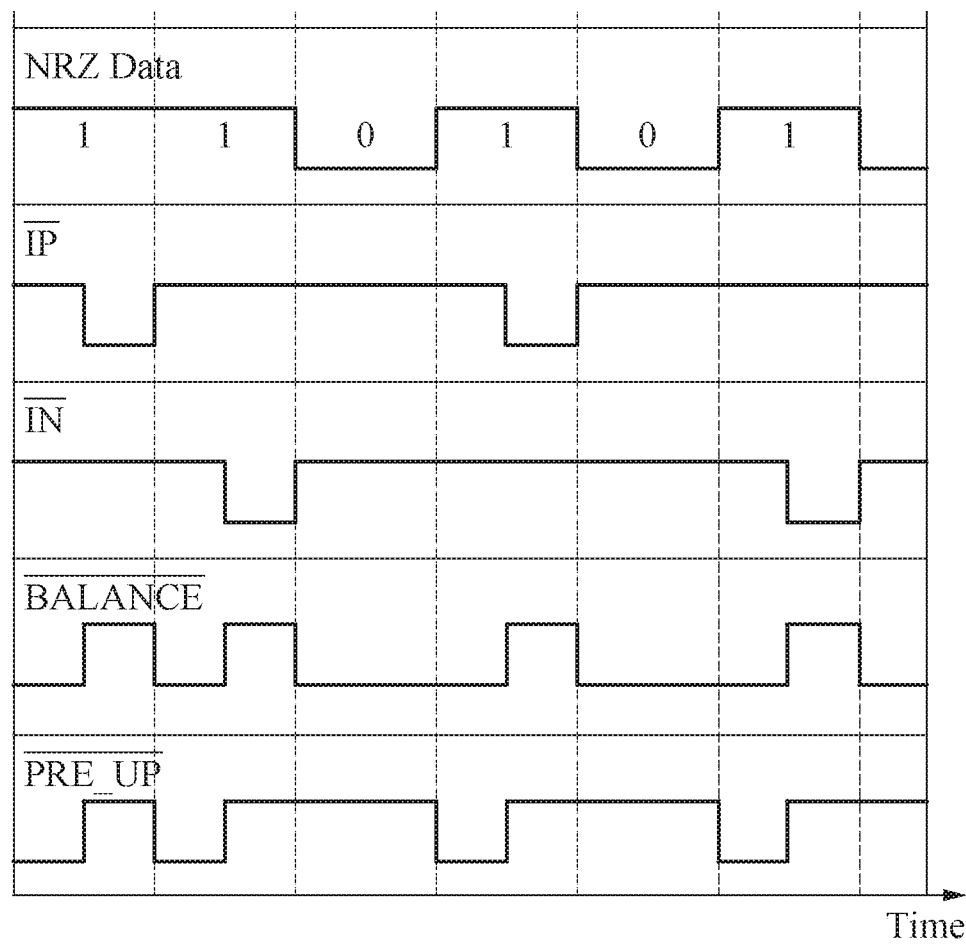
FIG. 8 illustrates an output signal of the RZ encoder shown in FIG. 5.

FIG. 7 is a circuit diagram illustrating an example of the RZ encoder shown in FIG. 5, and FIG. 8 illustrates an output signal of the RZ encoder shown in FIG. 5.

The RZ encoder 300 may encode an input signal (for example, NRZ Data) to generate an encoded signal and/or a control signal. For example, the RZ encoder 300 may generate the encoded signal and/or the control signal based on the input signal and a clock signal CLK.

The encoded signal may include a first encoded signal $\overline{IP}$ and a second encoded signal $\overline{IN}$.

The first encoded signal $\overline{IP}$ may correspond to a positive pulse of the RZ signal. For example, in the RZ signal, a binary "1" encoded to a positive current may be generated based on the first encoded signal $\overline{IP}$.

The second encoded signal $\overline{IN}$ may correspond to a negative pulse of the RZ signal. For example, in the RZ signal, a binary "1" encoded to a negative current may be generated based on the second encoded signal $\overline{IN}$.

The control signal may include a first control signal $\overline{BALANCE}$ and/or a second control signal $\overline{PRE\_UP}$.

The channel driver 400 may perform passive charge balancing based on the first control signal $\overline{BALANCE}$. For example, the channel driver 400 may remove charge remaining in biological tissue using the first control signal $\overline{BALANCE}$.

The second control signal $\overline{PRE\_UP}$ may activate or deactivate a current source of the channel driver 400. For example, the second control signal $\overline{PRE\_UP}$ may activate the current source only if necessary, thereby efficiently using power. The second control signal $\overline{PRE\_UP}$ may be an activation signal for the current source.

Figure 9:
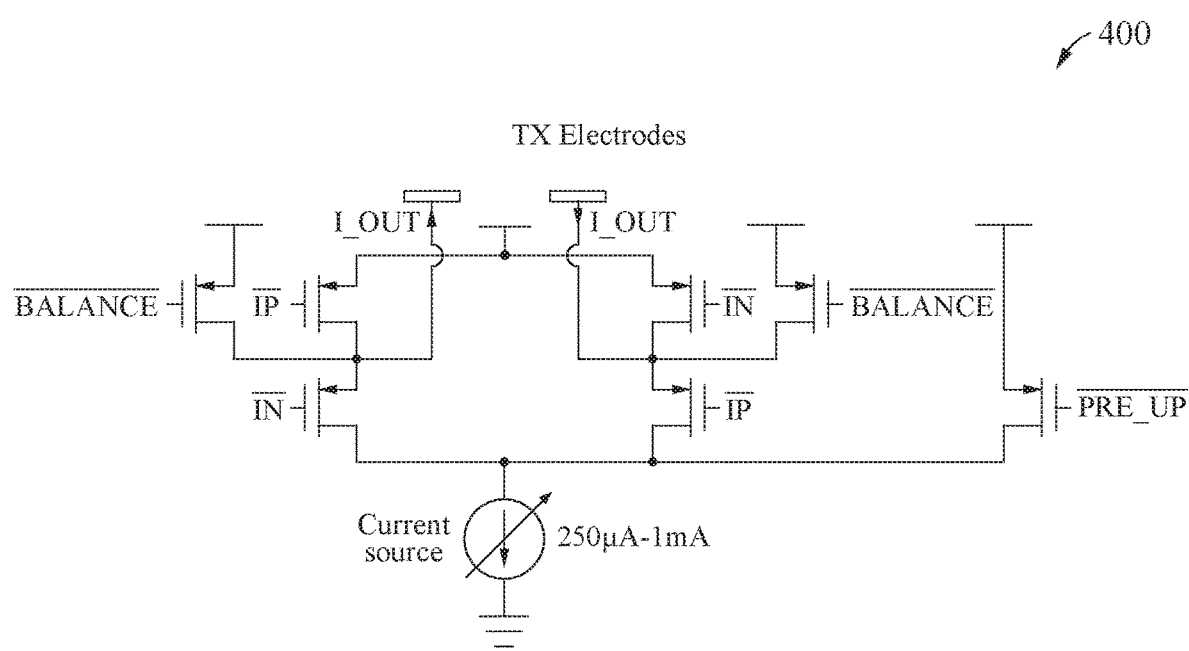
FIG. 9 is a circuit diagram illustrating an example of a channel driver shown in FIG. 5.

FIG. 9 is a circuit diagram illustrating an example of the channel driver shown in FIG. 5.

In FIG. 9, the channel driver 400 is implemented using a plurality of p-type metal oxide semiconductors (PMOS) and the current source. However, example embodiments are not limited thereto, and the channel driver 400 may be implemented using NMOS instead of PMOS.

The channel driver 400 may generate an RZ signal I_OUT-I_OUT of a biphasic waveform based on the first encoded signal $\overline{IP}$, the second encoded signal $\overline{IN}$, the first control signal $\overline{BALANCE}$, and/or the second control signal $\overline{PRE\_UP}$.

The channel driver 400 may provide a function for the human-body safety.

The channel driver 400 may regulate the magnitude of current injected into a human body. Also, the channel driver 400 may perform 1st-order charge balancing to reduce the amount of charge remaining in the biological tissue using the RZ signal I_OUT-I_OUT of the biphasic waveform. Further, the channel driver 400 may remove the remaining charge from the biological tissue by performing passive charge balancing using the first control signal $\overline{BALANCE}$.

The channel driver 400 may reduce the power consumption by using the second control signal $\overline{PRE\_UP}$. For example, the second control signal $\overline{PRE\_UP}$ may activate the current source only if necessary, thereby reducing the power consumption. The channel driver 400 may reduce the power consumption by 36.8%, when compared to a conventional current-mode channel driver.

FIGS. 10A through 10E illustrate an operation of the channel driver shown in FIG. 5. The operation of the channel driver will be described in detail with reference to the drawings.

Figure 10A:
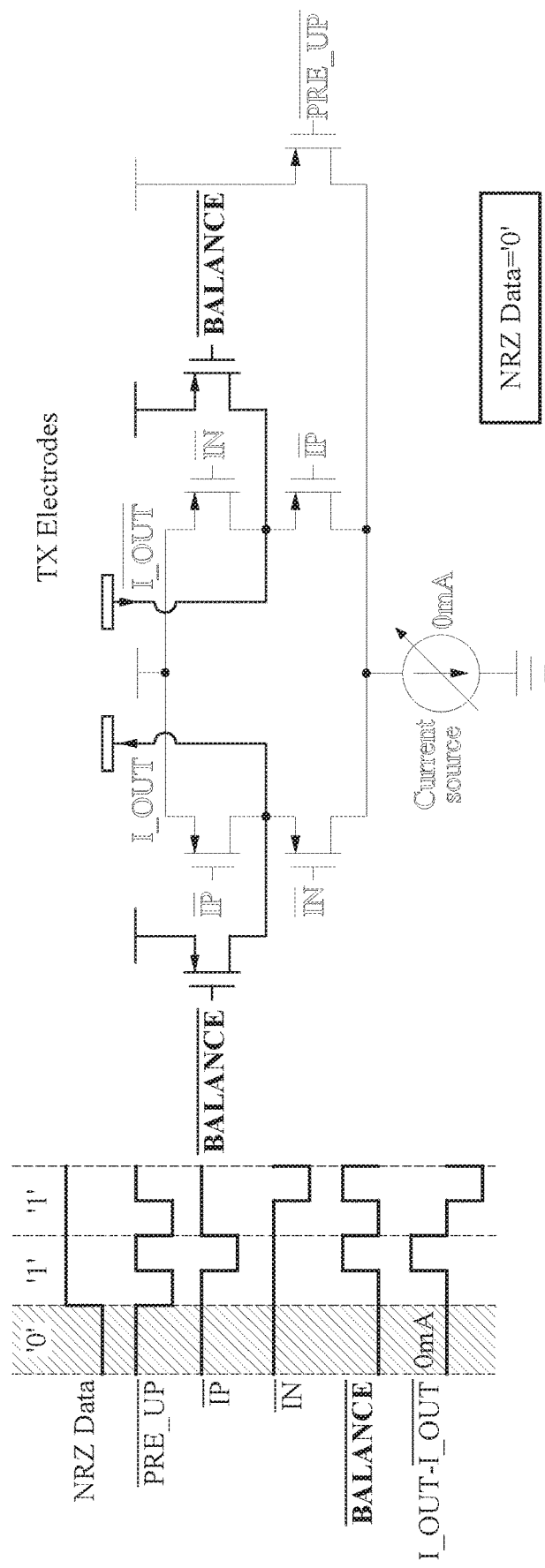
FIGS. 10A through 10E illustrate an operation of the channel driver shown in FIG. 5.

FIG. 10A illustrates the operation of the channel driver 400 if an input signal NRZ Data is binary "0".

If the input signal NRZ Data is binary "0", the channel driver 400 may deactivate the current source to save power. In addition, the channel driver 400 may remove residual charges by performing charge balancing using the first control signal $\overline{BALANCE}$ and reduce the possibility of damage to biological tissues.

Figure 10B:
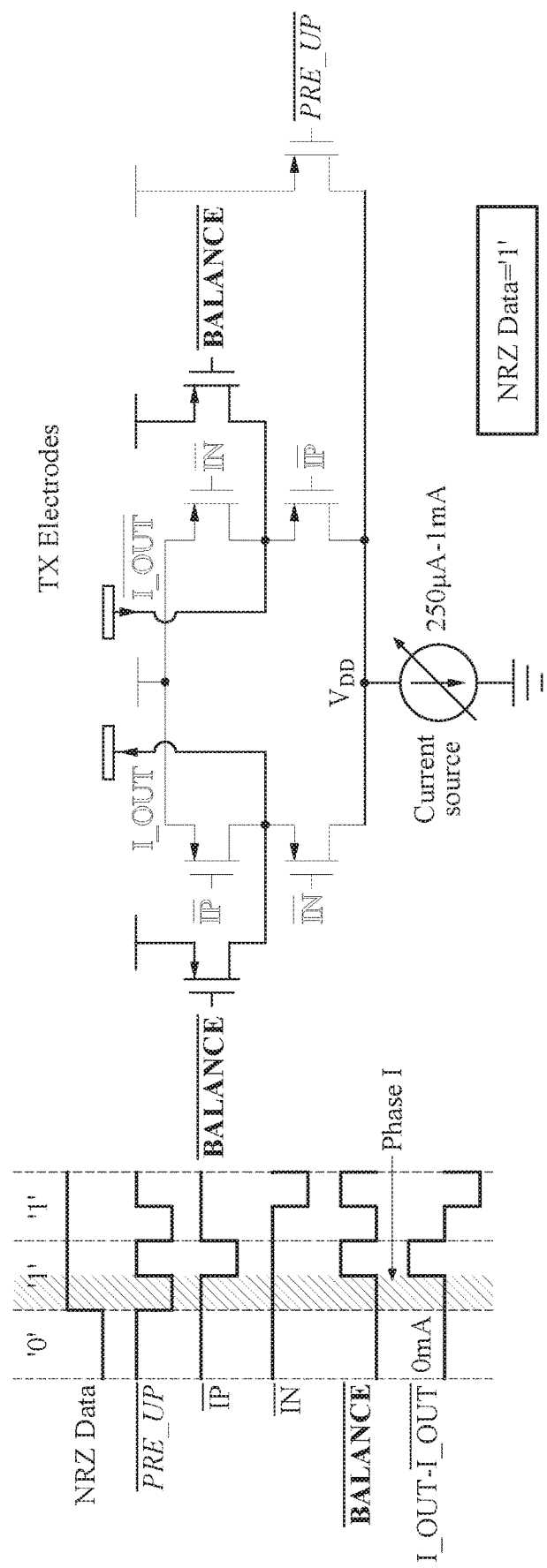

FIG. 10B illustrates the operation of the channel driver 400 in a preceding half cycle (hereinafter, phase I) of binary "1" of the input signal NRZ Data.

In phase I, the channel driver 400 may pre-charge a drain of the current source to apply a current correctly during the following half cycle (hereinafter, phase II). For example, the channel driver 400 may charge the current source based on the second control signal $\overline{PRE\_UP}$.

Since the channel driver 400 has not yet applied a current, charge balancing may be still performed.

Figure 10C:
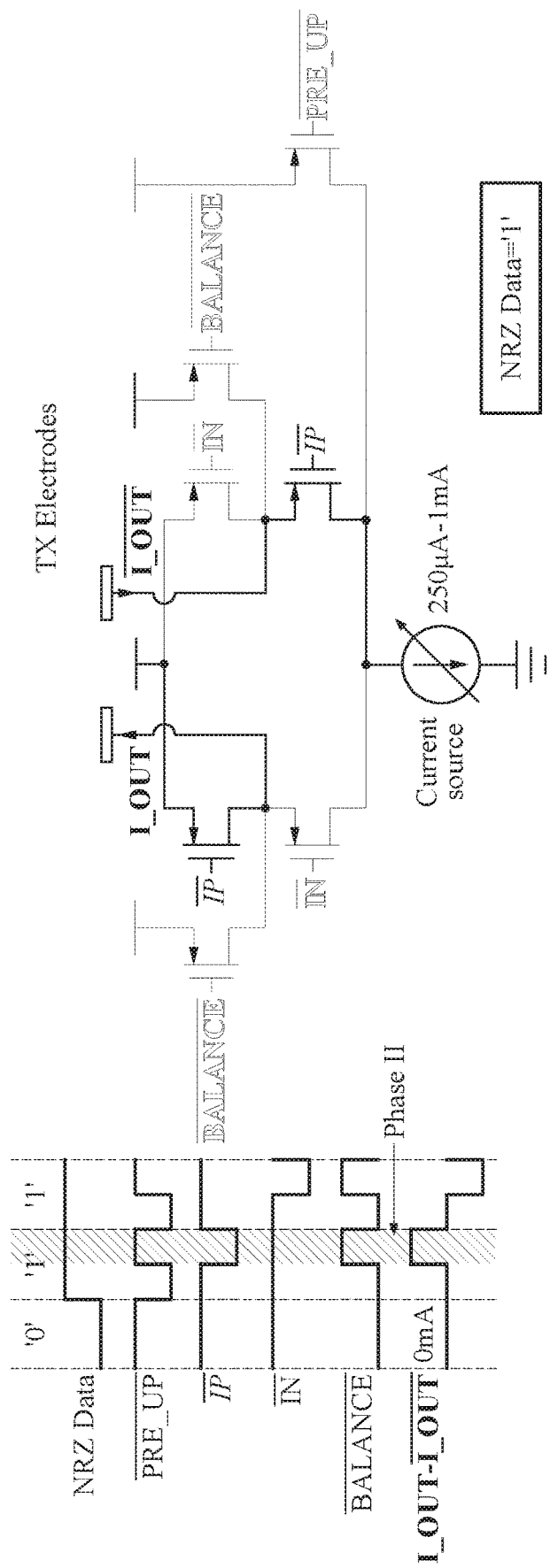

FIG. 10C illustrates the operation of the channel driver 400 in phase II.

In phase II, the channel driver 400 may connect a positive current path. For example, the channel driver 400 may apply the first encoded signal $\overline{IP}$ to an electrode, such that the RZ signal I_OUT-I_OUT becomes positive binary "1". That is, the channel driver 400 may apply a positive current to the body channel based on the first encoded signal $\overline{IP}$.

Since the RZ signal I_OUT-I_OUT is of a biphasic waveform, the RZ signal should be negative binary "1" after positive binary "1" when the input signal NRZ Data is binary "1". That is, the channel driver 400 needs to apply a negative current to the body channel.

Figure 10D:
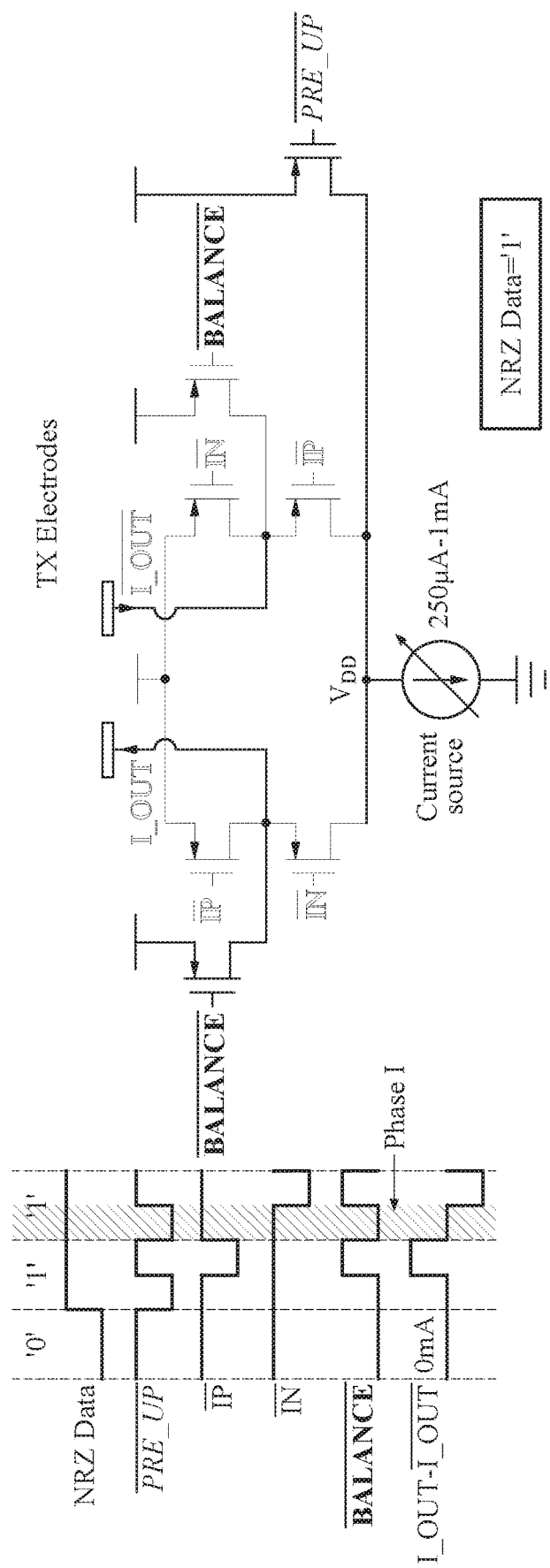

FIG. 10D illustrates the operation of the channel driver 400 in phase I when applying a negative current.

As in phase I before applying a negative current, the channel driver 400 may charge the current source based on the second control signal $\overline{PRE\_UP}$. Further, the channel driver 400 may perform charge balancing using the first control signal $\overline{BALANCE}$.

Figure 10E:
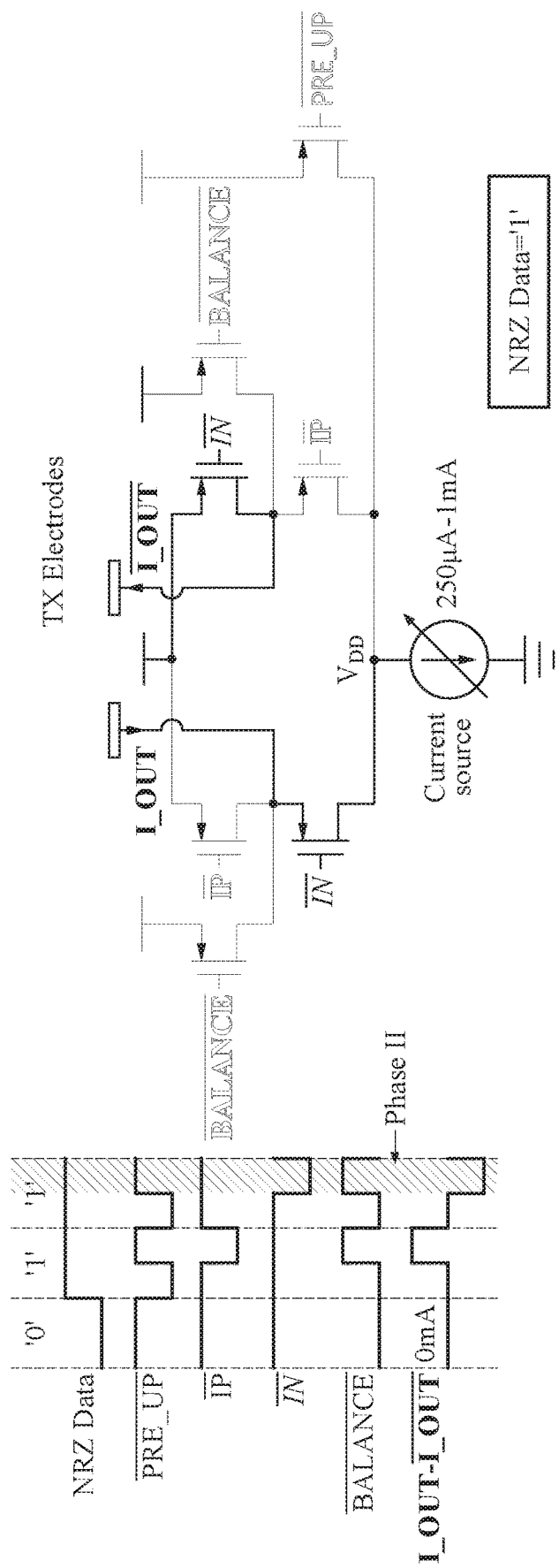

FIG. 10E illustrates the operation of the channel driver 400 in phase II when applying a negative current.

The channel driver 400 may enable the RZ signal I_OUT-I_OUT to have negative binary "1" based on the second encoded signal $\overline{IN}$. For example, the channel driver 400 may apply a negative current to the body channel by applying the second encoded signal $\overline{IN}$ to the electrode.

Figure 11:
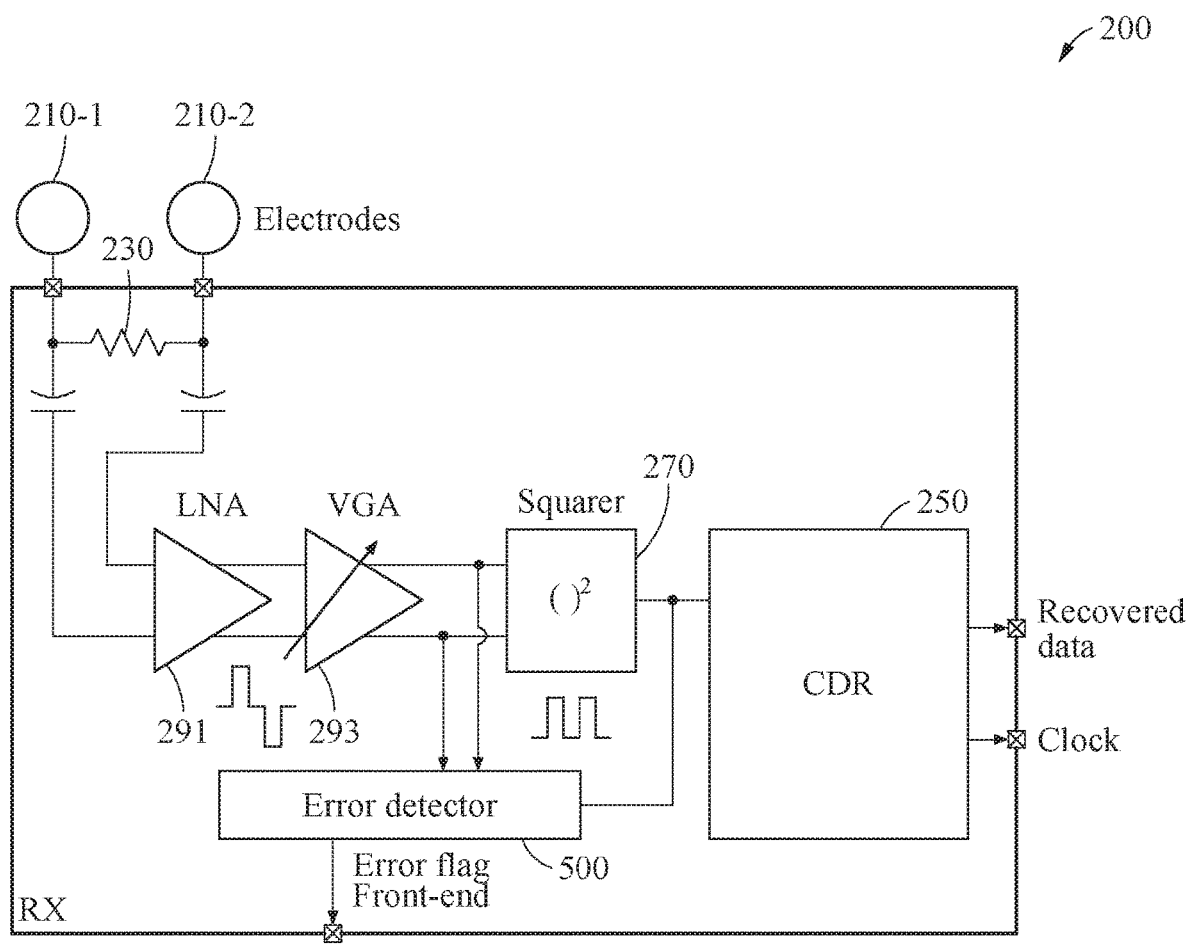
FIG. 11 is a circuit diagram illustrating an example of a receiver shown in FIG. 4.

FIG. 11 is a circuit diagram illustrating an example of the receiver shown in FIG. 4.

The receiver 200 may include a pair of electrodes 210-1 and 210-2, a termination 230, a clock and data recovery (CDR) circuit 250, a squarer 270, a low-noise amplifier (LNA) 291, a variable-gain amplifier (VGA) 293, and an error detector 500.

The pair of electrodes 210-1 and 210-2 may receive a signal transmitted by the transmitter 100 through a body channel. For example, the pair of electrodes 210-1 and 210-2 may receive an RZ signal of a biphasic waveform.

The termination 230 may flatten a channel response. For example, the termination 230 may widen the bandwidth by flattening the channel response.

The LNA 291 and the VGA 293 may amplify the input signal. For example, the LNA 291 and the VGA 293 may amplify the RZ signal.

The squarer 270 may square the input signal and output the squared signal. For example, the squarer 270 may convert the biphasic waveform into a monophasic waveform, such that a comparator may-make decision with a single threshold voltage.

The CDR 250 may recover a clock and decode data. For example, the CDR 250 may recover the clock and restore the data based on the RZ signal received from the transmitter 100.

The CDR 250 may extract clock information based on transitions of binary "1" of the bipolar RZ signal. In addition, since the data information appears during a half cycle, the CDR 250 may recover a 100-MHz clock signal using a half-rate bang-bang CDR.

The CDR 250 may decrypt the data based on the restored clock signal. In a locked condition, a clock signal with a 90-degree phase is aligned to the position of a data transition.

Thus, the CDR 250 may decode the data by performing X-OR gating of the two comparator outputs at the 0-degree phase and the 180-degree phase.

The error detector 500 may detect an error in the received bipolar RZ signal. The error detector 500 may detect a frequency of error occurrence, and the robot arm may check a channel state based on the frequency of error occurrence and determine whether additional channel coding is necessary at the cost of higher power and lower effective data rate.

Figure 12:
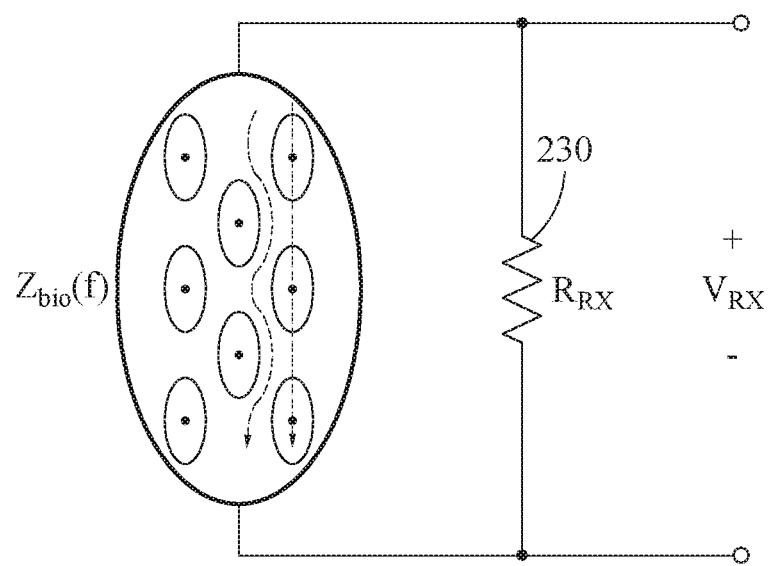
FIGS. 12 and 13 illustrate an operation of a termination shown in FIG. 11.
Figure 13:
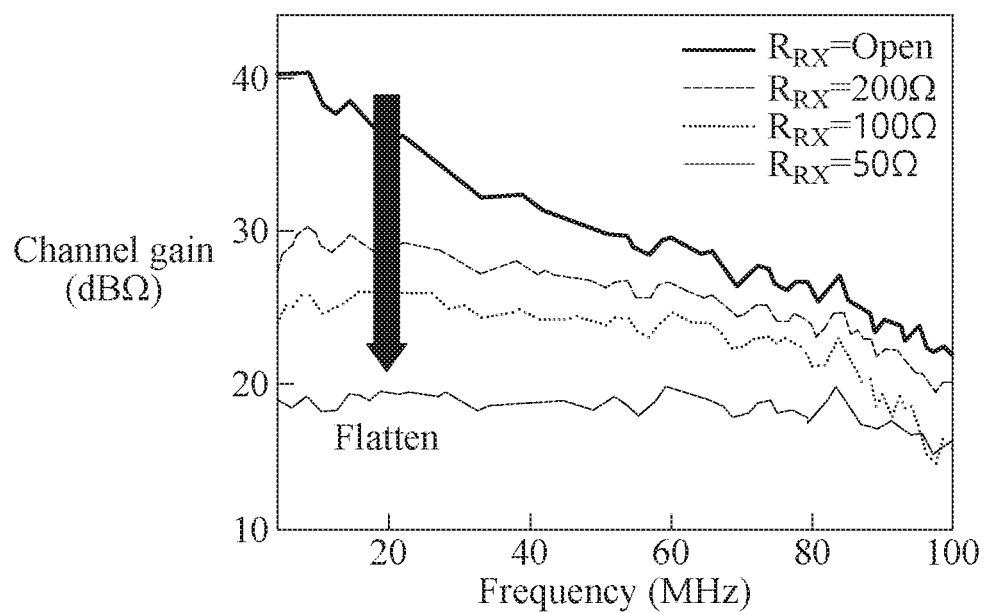

FIGS. 12 and 13 illustrate an operation of the termination shown in FIG. 11.

When a termination $R_{RX}$ is applied to the input of the receiver 200, the channel impedance may be calculated based on parallel values of the bioimpedance and the termination impedance.

A difference in channel gain between a low frequency and a high frequency may be reduced through paralleling. For example, a flatter channel response may be obtained by applying the termination $R_{RX}$.

The receiver 200 may acquire a 100-MHz channel bandwidth using the termination $R_{RX}$ of 50 to 100 ohm.

Figure 14:
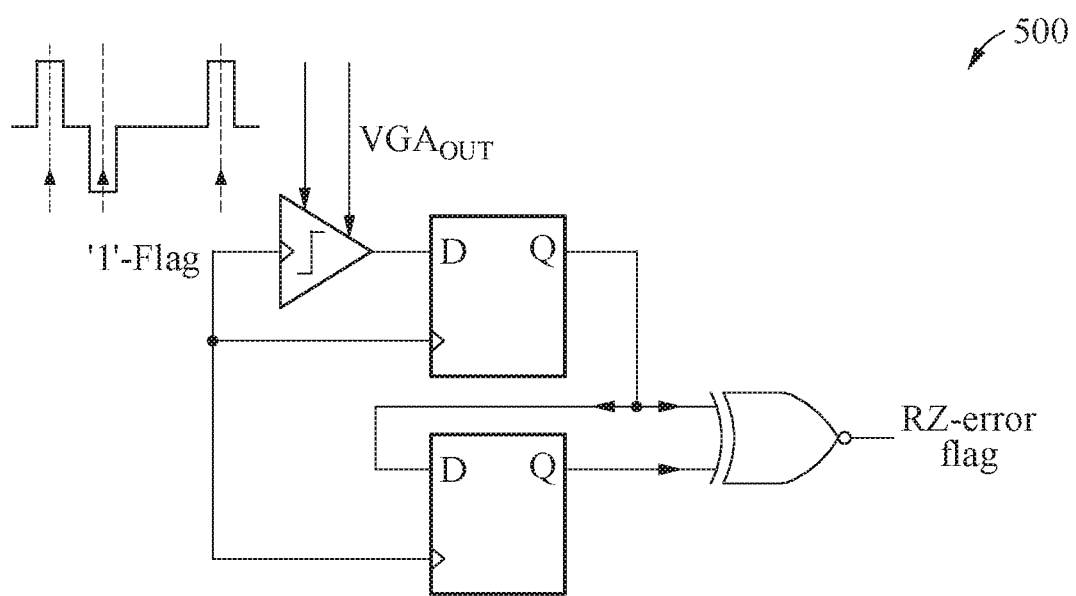
FIG. 14 is a circuit diagram illustrating an example of an error detector shown in FIG. 11.
Figure 15A:
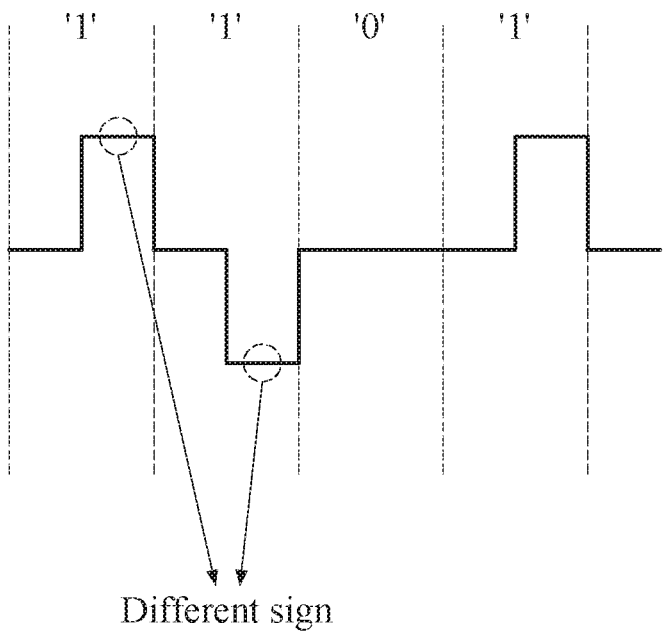
FIGS. 15A through 15D illustrate an operation of the error detector shown in FIG. 11.
Figure 15B:
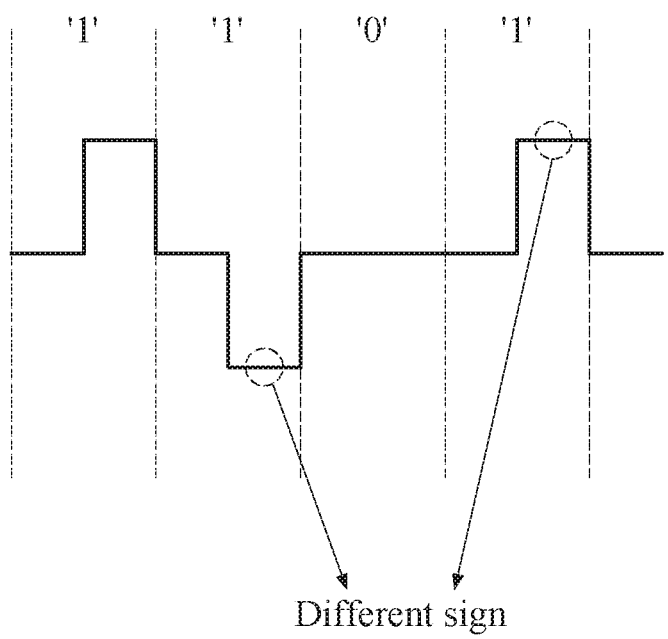
Figure 15C:
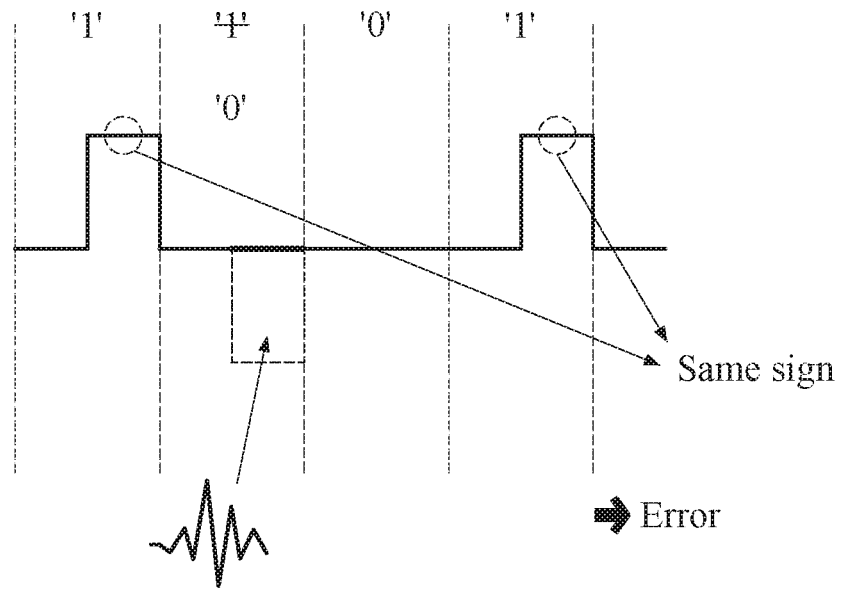
Figure 15D:
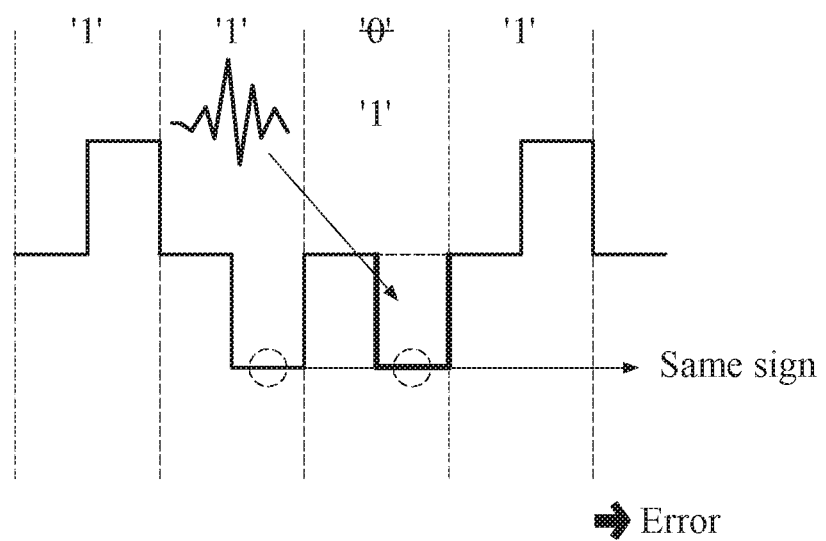

FIG. 14 is a circuit diagram illustrating an example of the error detector shown in FIG. 11, and FIGS. 15A through 15D illustrate an operation of the error detector shown in FIG. 11.

FIG. 14 illustrates an example of the error detector 500, which may be implemented in various manners to perform the same function.

Consecutive binary "1"s of the RZ signal transmitted by the transmitter 100 should have different signs. Thus, the RZ signal received by the receiver 200 also needs to have consecutive binary "1"s with different signs.

That is, neighboring pulses of the RZ signal received by the receiver 200 do not have the same sign unless the data is corrupted at the channel.

Thus, the error detector 500 may detect an error by comparing a previous pulse and a current pulse of the input signal.

The error detector 500 may operate only when binary "1" is detected in the input signal. For example, the error detector 500 may detect a pulse of the input signal based on the output signal of the squarer 270, and may operate only when a pulse is detected. Therefore, the error detector 500 may consume only 60 μW.

Figure 16:
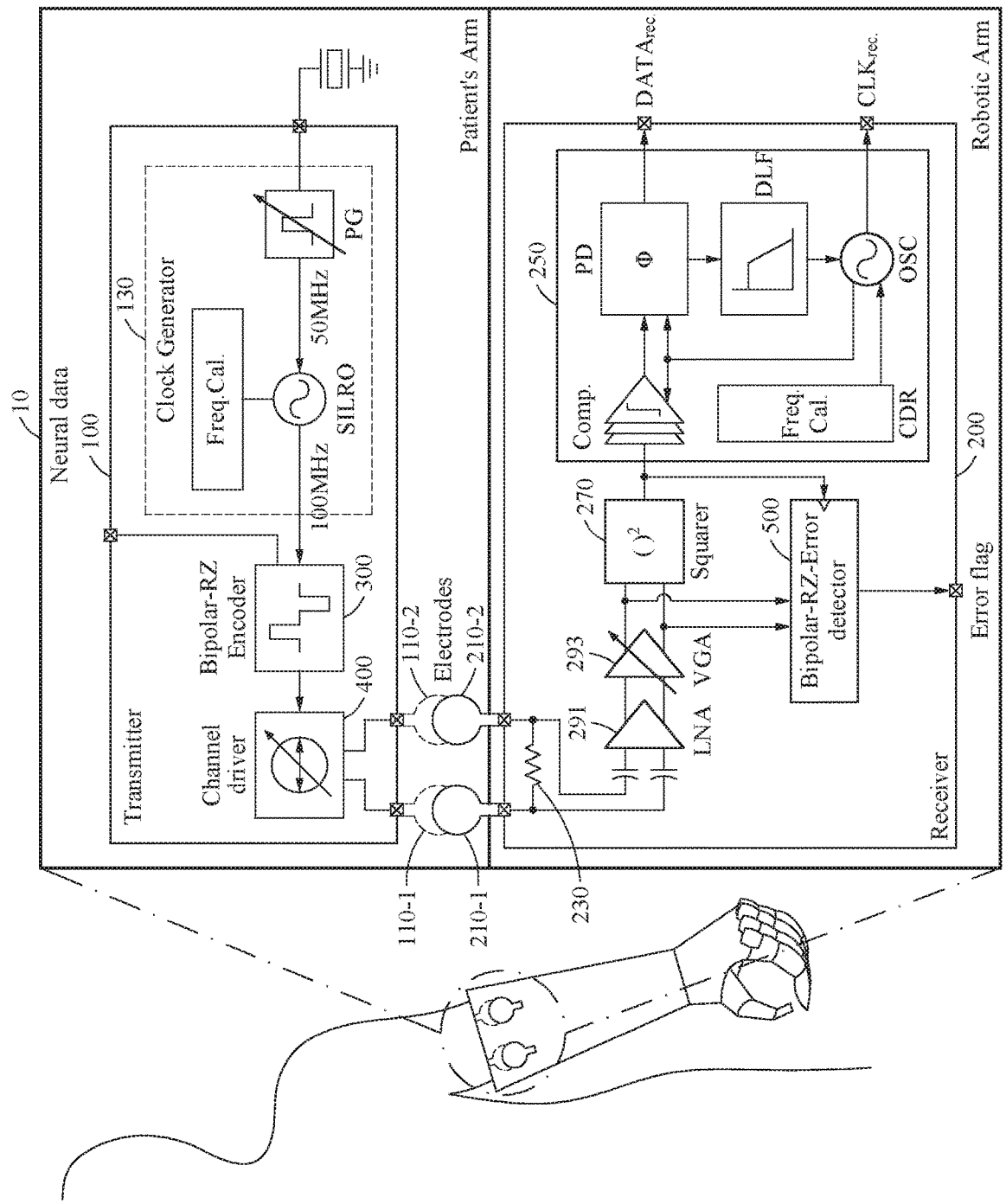
FIG. 16 illustrates the communication system of FIG. 4.

FIG. 16 illustrates the communication system of FIG. 4.

A bionic arm may include a detachable robot arm and an implantable IC to be implanted into a body of a user.

The implantable IC may include the transmitter 100. The transmitter 100 may encode a digitized signal of a neural signal generated at a major peripheral nerve into a bipolar RZ signal and transmit the bipolar RZ signal to the receiver 200 through a body channel.

The robot arm may include the receiver 200. The receiver 200 may receive and decode the bipolar RZ signal transmitted by the transmitter 100. The robot arm may operate based on the decoded data.

The receiver 200 may detect an error in the received signal, and may use a wide bandwidth by applying a termination.

The transmitter 100 and the receiver 200 may maintain a communication state through the uplink implemented with wideband GC-BCC even if the electrodes are misaligned, and may have a high data rate and be implemented with low power. In addition, the transmitter 100 and the receiver 200 may ensure the human-body safety by using the bipolar RZ signal.

The methods according to the above-described examples may be recorded in non-transitory computer-readable media including program instructions to implement various operations of the above-described examples. The media may also include, alone or in combination with the program instructions, data files, data structures, and the like. The program instructions recorded on the media may be those specially designed and constructed for the purposes of examples, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher-level code that may be executed by the computer using an interpreter. The above-described devices may be configured to act as one or more software modules in order to perform the operations of the above-described examples, or vice versa.

The software may include a computer program, a piece of code, an instruction, or some combination thereof, to independently or uniformly instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network-coupled computer systems so that the software is stored and executed in a distributed fashion. The software and data may be stored by one or more non-transitory computer-readable recording mediums.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

What is claimed is:

1. An operating method of an implantable transmitter, the operating method comprising:
   obtaining a neural input signal generated by a nerve of a human user, including biometric information;
   generating an encoded signal and a control signal by encoding the obtained neural input signal that includes the biometric information;
   generating a return-to-zero (RZ) signal of a biphasic waveform based on the encoded signal, the RZ signal including a zero signal between each data pulse of the generated RZ signal;
   transmitting, with the implantable transmitter, the RZ signal through a body channel of the human user to a device coupled to the human user; and
   performing passive charge balancing based on the control signal.

2. The operating method of claim 1, wherein the encoded signal comprises:
   a first encoded signal configured to generate a positive pulse of the RZ signal; and
   a second encoded signal configured to generate a negative pulse of the RZ signal.

3. The operating method of claim 1, further comprising: performing first-order charge balancing using the RZ signal.

4. The operating method of claim 1, wherein the generating of the RZ signal comprises generating the RZ signal using a current source.

5. The operating method of claim 4, wherein the control signal comprises an activation signal configured to activate or deactivate the current source.

6. An implantable transmitter for transmitting signals in a body channel of a human user, comprising:
   a memory configured to store a neural input signal generated by a nerve of the human user, including biometric information;
   a return-to-zero (RZ) encoder configured to generate an encoded signal and a control signal by encoding the neural input signal generated by the nerve of the human user;
   a channel driver configured to generate an RZ signal of a biphasic waveform based on the encoded signal, the RZ signal including a zero signal between each data pulse of the generated RZ signal; and
   an electrode configured to transmit the RZ signal through a body channel of the human user to a device coupled to the human user, and
   wherein the channel drier is configured to perform passive charge balancing based on the control signal.

7. The transmitter of claim 6, wherein the encoded signal comprises:
   a first encoded signal configured to generate a positive pulse of the RZ signal; and
   a second encoded signal configured to generate a negative pulse of the RZ signal.

8. The transmitter of claim 6, wherein the channel driver is configured to perform first-order charge balancing using the RZ signal.

9. The transmitter of claim 6, wherein the channel driver comprises a current source.

10. The transmitter of claim 9, wherein the control signal comprises an activation signal configured to activate or deactivate the current source.

* * * * *